United States Patent

Kennis et al.

[11] Patent Number: 6,057,325
[45] Date of Patent: May 2, 2000

[54] HEXAHYDRO-PYRIDO(4,3-B)INDOLE DERIVATIVES AS ANTIPSYCHOTIC DRUGS

[75] Inventors: Ludo Edmond Josephine Kennis, Turnhout; Josephus Carolus Mertens, Oud-Turnhout, both of Belgium

[73] Assignee: Janssen Pharmaceutia, N.V., Beerse, Belgium

[21] Appl. No.: 09/180,366

[22] PCT Filed: May 15, 1997

[86] PCT No.: PCT/EP97/02710

§ 371 Date: Nov. 9, 1998

§ 102(e) Date: Nov. 9, 1998

[87] PCT Pub. No.: WO97/44040

PCT Pub. Date: Nov. 27, 1997

[30] Foreign Application Priority Data

May 23, 1996 [EP] European Pat. Off. .............. 96201450

[51] Int. Cl.[7] ...................... A61K 31/513; A61K 31/519; C07D 471/04; C07D 519/00
[52] U.S. Cl. .......................... 514/258; 514/269; 544/278; 544/279; 544/281; 544/282; 544/311; 544/319; 544/321; 546/85; 546/86
[58] Field of Search ..................... 544/281, 282, 544/311, 319, 321, 278, 279, 28; 546/85, 86; 514/258, 269

[56] References Cited

U.S. PATENT DOCUMENTS 3,991,199  11/1976  Berger ...................... 544/316
4,337,250   6/1982  Welch et al. .............. 544/316

FOREIGN PATENT DOCUMENTS 24 57 305  12/1975  Germany .

OTHER PUBLICATIONS

Welch et al. Neuroleotics from the 4a,9b–trans–2,3,4,4a,5,9b–hexahJ. Med. Chem 29,2108–2111, 1986.
Welch et al. Neuroleotics from the 4a,9b–trans–2,3,4,4a,5,9b–hexa.. J.Med. Chem 29,2093–209908–2111, 1986.
Welch et al. 4a,9b–trans–8–fluoro–5–(fluorophenyl)–2–4–(4–fluoro–. . . J.Med. Chem 23, 994–952, 1980.
Nagai et al. Synthesis of 2,3,4,4a,5,9b–Hexahydro–1H–pyrido[4,3–b]..J.Med. Chem. 23, 677–683, 1979.
Nagai, Yasutake et al.: "Synthesis of 2,3,4,4a,5,9b–hexahydro–1H–yridol[4,3–b] in Dole Derivatives and Their Central Nervous System Activities", J. Med. Chem. (1979), 22(6), 677–83.

Primary Examiner—Mukund J. Shah
Assistant Examiner—V Balasubramanian
Attorney, Agent, or Firm—Mary A. Appollina

[57] ABSTRACT

This invention concerns the compounds of formula

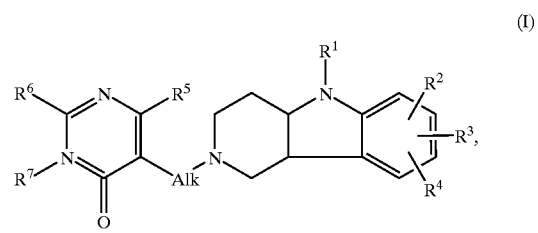

(I)

the pharmaceutically acceptable addition salts and the stereochemically isomeric forms thereof, wherein Alk is $C_{1-6}$alkanediyl; $R^1$ is hydrogen, $C_{1-6}$alkyl, aryl or aryl $C_{1-6}$alkyl; $R^2$, $R^3$ and $R^4$ are each independently selected from hydrogen, halo, hydroxy, nitro, cyano, $C_{1-6}$alkyl, $C_{1-6}$alkyloxy, trifluoromethyl, $C_{1-6}$alkylthio, mercapto, amino, mono- and di($C_{1-6}$alkyl)amino, carboxyl, $C_{1-6}$alkyloxycarbonyl or $C_{1-6}$alkylcarbonyl; $R^5$ is hydrogen, $C_{1-6}$alkyl, phenyl or phenyl$C_{1-6}$alkyl; $R^6$ is hydrogen, $C_{1-6}$alkyl, $C_{1-6}$alkyloxy, $C_{1-6}$alkylthio, or a radical of formula $-NR^8R^9$, wherein $R^8$ and $R^9$ are each independently selected from hydrogen, $C_{1-6}$alkyl, phenyl or phenyl$C_{1-6}$alkyl; $R^7$ is hydrogen or $C_{1-6}$alkyl; or $R^6$ and $R^7$ taken together may form a bivalent radical of formula $-R^6-R^7-$; having central dopamine and serotonin antogonistic activity; their preparation, compositions containing them and their use as a medicine.

10 Claims, No Drawings

HEXAHYDRO-PYRIDO(4,3-B)INDOLE DERIVATIVES AS ANTIPSYCHOTIC DRUGS

CROSS REFERENCE TO RELATED APPLICATIONS

This application is a National Stage application under 35 U.S.C. § 371 of PCT/EP97/02710 filed May 15, 1997, which claims priority from EP 96.201.450.2, filed May 23, 1996.

This invention relates to hexahydro-pyrido[4,3-b]indole derivatives having therapeutic potential in psychotic disorders, and processes for their preparation; it further relates to compositions comprising these derivatives, as well as their use as a medicine.

A number of hexahydro-pyrido[4,3-b]indole compounds substituted on the 2-position with an alkyl group bearing a substituted phenyl and an hydroxy, which have antipsychotic properties as evidenced by their ability to block the action of dopamine receptors of the central nervous system, are disclosed in J. Med. Chem. 22:677–683 (1979) and J. Med. Chem. 29:2093–2099 (1986). J. Med. Chem. 23:949–952 (1980) describes 4a,9b-trans-8-fluoro-5-(4-fluorophenyl)-2-[4-(4-fluorophenyl)-4-hydroxy-butyl]-2,3,4,4a,5,9b-hexahydro-1H-pyrido[4,3-b]indole hydrochloride as a neuroleptic agent capable of blocking dopamine receptors.

The problem which this invention sets out to solve is to provide compounds having besides central dopamine antagonistic activity also central serotonin antagonistic activity at the same dosage, a combination which is considered advantageous in potential antipsychotic drugs.

The compounds of the present invention differ from the cited art compounds structurally, by the fact that the tricyclic hexahydro-pyrido[4,3-b]indole moiety, also known as a hexahydro γ-carboline moiety, is invariably substituted on the 2-position with an alkyl group bearing a pyrimidinyl derivative, and by their favourable pharmacological properties, in particular by the fact that in addition to their excellent central dopamine antagonistic activity the compounds of the present invention also have potent central serotonin antagonistic activity.

The present invention concerns the compounds of formula

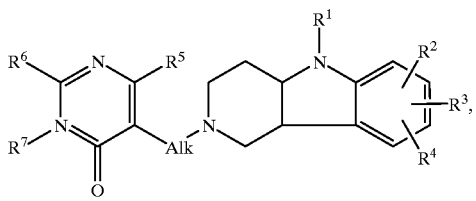

(I)

the N-oxide forms, the pharmaceutically acceptable addition salts and the stereochemically isomeric forms thereof, wherein Alk is $C_{1-6}$alkanediyl;

$R^1$ is hydrogen, $C_{1-6}$alkyl, aryl or aryl$C_{1-6}$alkyl;

$R^2$, $R^3$ and $R^4$ are each independently selected from hydrogen, halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl;

$R^5$ is hydrogen, $C_{1-6}$alkyl, phenyl or phenyl$C_{1-6}$alkyl;

$R^6$ is hydrogen, $C_{1-6}$alkyl, $C_{1-6}$alkyloxy, $C_{1-6}$alkylthio, or a radical of formula —$NR^8R^9$, wherein $R^8$ and $R^9$ are each independently selected from hydrogen, $C_{1-6}$alkyl, phenyl or phenyl$C_{1-6}$alkyl;

$R^7$ is hydrogen or $C_{1-6}$alkyl; or $R^6$ and $R^7$ taken together may form a bivalent radical of formula —$R^6$—$R^7$—, wherein —$R^6$—$R^7$— represents

| | |
|---|---|
| —CH$_2$—CH$_2$—CH$_2$— | (a-1), |
| —CH$_2$—CH$_2$—CH$_2$—CH$_2$— | (a-2), |
| —CH=CH—CH$_2$— | (a-3), |
| —CH$_2$—CH=CH— | (a-4) or |
| —CH=CH—CH=CH— | (a-5); | wherein one or two hydrogen atoms of said radicals (a-1) to (a-5) each independently may be replaced by halo, $C_{1-6}$alkyl, aryl$C_{1-6}$alkyl, trifluoromethyl, amino, hydroxy, $C_{1-6}$alkyloxy or $C_{1-10}$alkylcarbonyloxy; or where possible, two geminal hydrogen atoms may be replaced by $C_{1-6}$alkylidene or aryl$C_{1-6}$alkylidene; or —$R^6$—$R^7$— may also be

| | |
|---|---|
| —S—CH$_2$—CH$_2$— | (a-6), |
| —S—CH$_2$—CH$_2$—CH$_2$— | (a-7), |
| —S—CH=CH— | (a-8), |
| —NH—CH$_2$—CH$_2$— | (a-9), |
| —NH—CH$_2$—CH$_2$—CH$_2$— | (a-10), |
| —NH—CH=CH— | (a-11), |
| —NH—CH=N— | (a-12), |
| —S—CH=N— | (a-13) or |
| —CH=CH—O— | (a-14); | wherein one or where possible two or three hydrogen atoms in said radicals (a-6) to (a-14) each independently may be replaced by $C_{1-6}$alkyl or aryl; and aryl is phenyl or phenyl substituted with one, two or three substituents selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

As used in the foregoing definitions and hereinafter, halo is generic to fluoro, chloro, bromo and iodo; $C_{1-6}$alkyl defines straight and branched chain saturated hydrocarbon radicals having from 1 to 6 carbon atoms such as, for example, methyl, ethyl, propyl, butyl, 1-methylethyl, 2-methylpropyl, 2,2-dimethylethyl, pentyl, hexyl, 3-methylbutyl, 2-methylpentyl and the like; $C_{1-10}$alkyl is meant to comprise $C_{1-6}$alkyl and the higher homologues thereof having from 7 to 10 carbon atoms such as, for example, heptyl, octyl, nonyl, decyl and the like; $C_{1-2}$alkanediyl defines bivalent straight chain saturated hydrocarbon radicals having 1 or 2 carbon atoms such as, for example, methylene and 1,2-ethanediyl; $C_{1-6}$alkanediyl is meant to comprise $C_{1-2}$alkanediyl and the higher straight and branched chain saturated hydrocarbon homologues thereof having from 3 to 6 carbon atoms such as, for example, 1,3-propanediyl, 1,4-butanediyl, 1,5-pentanediyl, 1,6-hexanediyl and the like; the term $C_{1-6}$alkylidene defines bivalent straight or branch chained alkylidene radicals having from 1 to 6 carbon atoms such as, for example, methylene, ethylidene, 1-propylidene, 1-butylidene, 1-pentylidene, 1-hexylidene and the like.

The pharmaceutically acceptable addition salts as mentioned hereinabove are meant to comprise the therapeutically active non-toxic acid and non-toxic base addition salt forms which the compounds of formula (I) are able to form.

The compounds of formula (I) which appear in their free form as a base can be converted in their acid addition salt by treating said free base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which appear in their free form as an acid, i.e. having at least one acidic proton, may be converted in their pharmaceutically acceptable base addition salts by treating said free acid form with a suitable organic or inorganic base. Appropriate base salt forms comprise, for example, the ammonium salts, the alkali and earth alkaline metal salts, e.g. the lithium. sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture, and in particular the racemic mixture, of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

The numbering of the tricyclic ring-system present in the compounds of formula (I), as defined by Chemical Abstracts nomenclature is shown in formula (I')

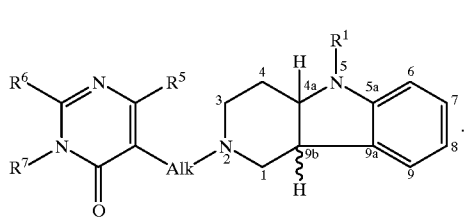

(I')

The compounds of formula (I) occur as "cis" or "trans" isomers. Said terms refer to the configuration of the hydrogen atoms on carbon atoms 4a and 9b of the hexahydropyrido[4,3-b]indole moiety and are in accordance with Chemical Abstracts nomenclature. When both hydrogen atoms are on the same side of the mean plane determined by the hexahydro-pyrido[4,3-b]indole moiety then the configuration is designated "cis", if not, the configuration is designated "trans".

The N-oxide forms of the compounds of formula (I) are meant to comprise those compounds of formula (I) wherein one or several nitrogen atoms are oxidized to the so-called N-oxide.

A special group of compounds are those compounds of formula (I) wherein one or two hydrogen atoms of the radicals (a-1) to (a-5) each independently are replaced by $C_{1-6}$alkyl, $C_{1-6}$alkyloxy, hydroxy or $C_{1-10}$alkylcarbonyloxy; and one or where possible two hydrogen atoms in the radicals (a-6) to (a-14) each independently are replaced by $C_{1-6}$alkyl.

A group of interesting compounds are those compounds of formula (I) wherein $R^6$ and $R^7$ are taken together to form a bivalent radical of formula —$R^6$—$R^7$—, in particular a bivalent radical of formula (a-1), (a-5), (a-6) or (a-8) wherein one of the hydrogen atoms may be replaced by $C_{1-6}$alkyl, in particular methyl; and $R^5$ is phenyl or $C_{1-6}$alkyl and preferably is methyl.

A particular group of compounds are those compounds of formula (I) wherein Alk is $C_{1-2}$alkanediyl.

Another particular group of compounds are those compounds of formula (I) wherein $R^1$ is hydrogen, $C_{1-6}$alkyl or phenyl substituted with halo.

Still another particular group of compounds are those compounds of formula (I) wherein $R^2$ is halo or $C_{1-6}$alkyloxy, in particular methoxy; and $R^3$ and $R^4$ are hydrogen.

Preferred compounds are those compounds of formula (I) wherein the configuration between the hydrogen atom on carbon atom 4a and the hydrogen atom on carbon atom 9b of the hexahydro-pyrido[4,3-b]indole moiety is defined as trans.

More preferred compounds of formula (I) are those wherein $R^1$ is hydrogen, $R^2$ is halo and is located on the 8-position of the hexahydro-pyrido[4,3-b]indole moiety, $R^3$ and $R^4$ are both hydrogen; Alk is $C_{1-2}$alkanediyl, $R^5$ is phenyl or methyl; and $R^6$ and $R^7$ are taken together to form a bivalent radical of formula —$R^6$—$R^7$—, in particular a bivalent radical of formula (a-1), (a-5), (a-6) or (a-8) wherein one of the hydrogen atoms may be replaced by methyl.

Most preferred compounds of formula (I) are
3-[2-(8-fluoro-1,3,4,4a,5,9b-hexahydro-2H-pyrido[4,3-b]indol-2-yl)ethyl]-2-methyl-4H-pyrido[1,2-a]pyrimidin-4-one;

6-[2-(8-fluoro-1,3,4,4a,5,9b-hexahydro-2H-pyrido[4,3-b]indol-2-yl)ethyl]-7-methyl-5H-thiazolo[3,2-a]pyrimidin-5-one; and 6-[2-(8-chloro-1,3,4,4a,5,9b-tetrahydro-2H-pyrido[4,3-b]indol-2-yl)ethyl]-7-methyl-5H-thiazolo[3,2-a]pyrimidin-5-one; the stereoisomeric forms and the pharmaceutically acceptable addition salts thereof, and also the N-oxide forms thereof.

The compounds of the present invention can generally be prepared by N-alkylating an intermediate of formula (II) with an intermediate of formula (III), wherein W is an appropriate leaving group such as, for example, chloro, bromo, methanesulfonyloxy or benzenesulfonyloxy. The reaction can be performed in a reaction-inert solvent such as, for example, toluene, dichloromethane, methyl isobutylketone or N,N-dimethyl-formamide, in the presence of a suitable base such as, for example, sodium carbonate, sodium hydrogen carbonate or triethylamine, and optionally in the presence of potassium iodide. Stirring may enhance the rate of the reaction. The reaction may conveniently be carried out at a temperature ranging between room temperature and reflux temperature.

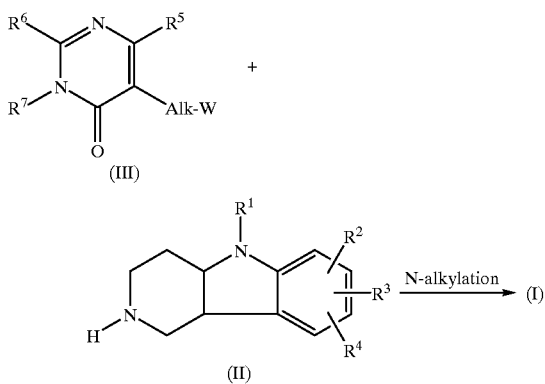

Compounds of formula (I) wherein the carbon atom of Alk by which it is attached to the nitrogen atom on the 2 position of the hexahydro-pyrido[4,3-b]indole moiety has at least one hydrogen atom, said compounds being represented by formula (I-a) and said Alk being represented by Alk'H, can be prepared by reductively N-alkylating an intermediate of formula (II) with an aldehyde or ketone of formula (IV), wherein the —Alk'=O moiety is derived from an —Alk'H$_2$ moiety by replacing two geminal hydrogen atoms by an oxo group, following art-known reductive N-alkylation procedures.

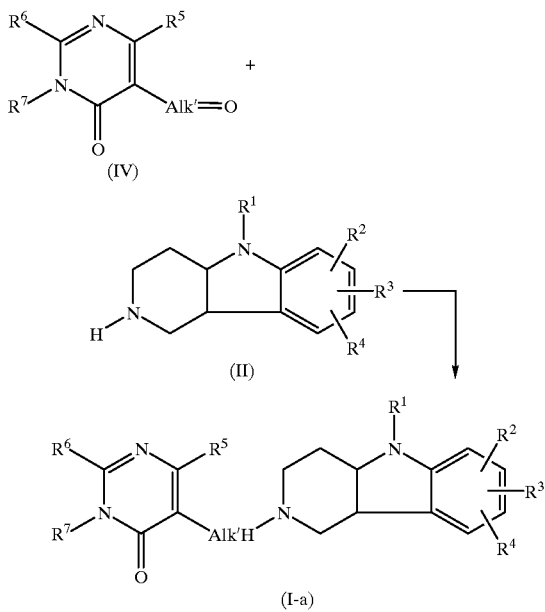

Said reductive N-alkylation may be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g. thiophene or quinoline-sulphur. To enhance the rate of the reaction, the temperature may be elevated in a range between room temperature and the reflux temperature of the reaction mixture and optionally the pressure of the hydrogen gas may be raised.

The compounds of formula (I) may further be prepared by converting compounds of formula (I) into each other according to art-known group transformation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The intermediates of formula (II) can generally be prepared as outlined in the following paragraphs. Some intermediates of formula (II) are art-known from *J. Med. Chem.* 22:677–683 (1979) and *J. Med. Chem.* 29:2093–2099 (1986).

For instance, intermediates of formula (II) can be prepared by hydrogenation of intermediates of formula (VI), wherein $R^1$ is hydrogen and P is a suitable protective group such as, e.g. benzyl, and subsequent removal of the protecting group P. For instance, when P is benzyl, P can be removed by catalytic hydrogenation with palladium-on-carbon in a reaction-inert solvent and in the presence of hydrogen.

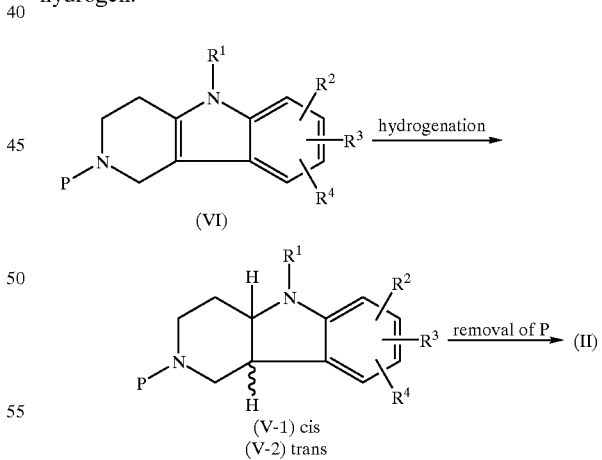

Said hydrogenation reaction can give intermediates of formula (V-1) wherein the configuration between the hydrogen atom on carbon atom 4a and the hydrogen atom on carbon atom 9b of the hexahydro-pyrido[4,3-b]indole moiety is defined as cis, when intermediates of formula (VI) are submitted to art-known catalytic hydrogenation procedures such as, e.g. stirring in a reaction-inert solvent, e.g. methanol or methanolic ammonia, in the presence of a suitable catalyst, e.g. Raney nickel or palladium-on-carbon and in the presence of hydrogen. To enhance the rate of the reaction, the temperature may be elevated in a range between room temperature and the reflux temperature of the reaction mixture and optionally the pressure of the hydrogen gas may be raised. Intermediates of formula (V-2) wherein the configuration between the hydrogen atom on carbon atom 4a and the hydrogen atom on carbon atom 9b of the hexahydro-pyrido[4,3-b]indole moiety is defined as trans, can be prepared by treating intermediates of formula (VI) with an appropriate reagent such as, e.g. $BH_3$-tetrahydrofuran complex in a reaction-inert solvent, e.g. tetrahydrofuran, as described in J. Med. Chem. 23:949–952 (1980); or $NaBH_4$ in a reaction-inert solvent, e.g. 2-methoxyethyl ether.

Intermediates of formula (V-a), defined as intermediates of formula (V) wherein $R^1$ is hydrogen, can be converted into intermediates of formula (V-b) wherein $R^{1'}$ is the same as $R^1$ but other than hydrogen, by submitting intermediates of formula (V-a) to art-known N-alkylation methods, as described herein above.

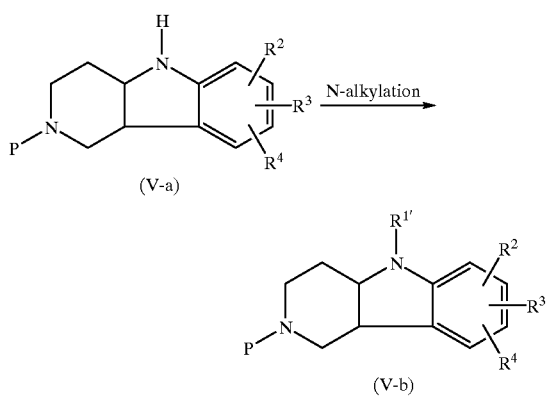

A number of intermediates and starting materials are known compounds which may be prepared according to art-known methodologies. For example, intermediates of formula (VI) and their preparations are described in J. Med. Chem. 9:436–438 (1966), J.C.S. (C) 1235 (1968), J. Org. Chem. 44:1063–1068 (1979) and J. Med. Chem. 23:635–643 (1980). Also, intermediates of formula (III) and their preparations are described in EP-A-0,037,265, EP-A-0,070,053, EP-A-0,110,435, EP-A-0,196,132 and EP-A-0,378,255.

Compounds of formula (I) and some of the intermediates in the present invention contain at least one asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. An alternative manner of separating the enantiomeric forms of the compounds of formula (I) and intermediates involves liquid chromatography, in particular liquid chromatography using a chiral stationary phase.

Pure stereochemically isomeric forms of the compounds of formula (I) may also be obtained from the pure stereochemically isomeric forms of the appropriate intermediates and starting materials, provided that the intervening reactions occur stereospecifically. The pure and mixed, in particular racemic, stereochemically isomeric forms of the compounds of formula (I) are intended to be embraced within the scope of the present invention.

The compounds of formula (I) display central dopamine antagonistic activity in combination with central serotonin antagonistic activity as can be seen in the "apomorphine, tryptamine, norepinephrine (ATN) test in rats", described in pharmacological example C.1. Centrally acting dopamine antagonists are potential antipsychotic drugs, in particular when simultaneously displaying serotonin antagonism. Moreover, most of the compounds lack relevant α-adrenergic antagonist activity in the norepinephrine test, suggesting absence of hypotensive activity.

The compounds of the present invention also show interesting pharmacological activity in the "mCPP Test on Rats", which test is described in WO 96/14320.

The compounds of formula (I), their pharmaceutically acceptable addition salts, stereochemically isomeric forms, or N-oxide forms thereof, are antagonists of the neurotransmitters dopamine and serotonin. Antagonizing said neurotransmitters will suppress or relieve a variety of symptoms associated with phenomena induced by the release, in particular the excessive release, of these neurotransmitters. Therapeutic indications for using the present compounds are mainly in the CNS area, especially psychotic disorders such as, e.g. schizophrenia, depression, neuroses, psychoses, bipolar disorders, aggressive behaviour, anxiety, migraine and the like. Further, serotonin is a potent broncho- and vasoconstrictor and thus the present antagonists may be used against hypertension and vascular disorders. In addition, serotonin antagonists have been associated with a number of other properties such as, the suppression of appetite and promotion of weight loss, which may prove effective in combatting obesity; and also the alleviation of withdrawal symptoms in addicts trying to discontinue drinking and smoking habits. The present compounds also appear to be useful therapeutic agents for combatting autism.

The present invention thus also relates to compounds of formula (I) as defined hereinabove for use as a medicine.

In view of the usefulness of the subject compounds in the treatment or prevention of disorders associated with the release, in particular the excessive release, of dopamine and/or serotonin, the present invention provides a method of treating warm-blooded animals suffering from such disorders, in particular psychotic disorders, said method comprising the systemic administration of a therapeutic effective amount of a compound of formula (I), a N-oxide or a pharmaceutically acceptable addition salt thereof, effective in treating disorders associated with the release or excessive release of dopamine and/or serotonin in particular psychotic disorders such as, e.g. schizophrenia, depression, neuroses, psychoses, bipolar disorders, aggressive behaviour, anxiety, migraine and the like.

For administration purposes, the subject compounds may be formulated into various pharmaceutical forms. To prepare the pharmaceutical compositions of this invention, a therapeutically effective amount of the particular compound, in addition salt or in free acid or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Addition salts of compounds of formula (I) due to their increased water solubility over the corresponding free base or free acid form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in the treatment of such disorders could determine the effective therapeutic daily amount from the test results presented hereinafter. An effective therapeutic daily amount would be from about 0.001 mg/kg to about 1 mg/kg body weight, more preferably from about 0.01 mg/kg to about 0.2 mg/kg body weight.

The following examples are intended to illustrate and not to limit the scope of the present invention.

Experimental Part

Hereinafter "THF" means tetrahydrofuran, "DIPE" means diisopropylether, "DCM" means dichloromethane, "DMF" means N,N-dimethylformamide and "ACN" means acetonitrile.

A. Preparation of the Intermediates.

EXAMPLE A.1

A mixture of ethyl 1,3,4,5-tetrahydro-2H-pyrido[4,3-b] indole-2-carboxylate (49.2 g), prepared as described in *J. Med. Chem.* 23:635–643 (1980), in $NH_3/CH_3OH$ (400 ml) was hydrogenated with Raney nickel (5 g) as a catalyst. The mixture was cooled and the catalyst was filtered off. The filtrate was evaporated. The residue was dissolved in anhydrous diethyl ether (600 ml) and HCl(g) was allowed to bubble through the solution for 30 minutes. The resulting precipitate was filtered off, dissolved in water (200 ml) and extracted with diethyl ether (100 ml). The organic layer was separated, dried, filtered and the solvent was evaporated. The residue was solidified in DIPE (150 ml), cooled to 0° C., filtered off and dried, yielding 34.3 g (70%) of (±)-ethyl cis-1,3,4,4a,5,9b-hexahydro-2H-pyrido[4,3-b]indole-2-carboxylate (intermediate 1).

EXAMPLE A.2

A mixture of intermediate 1 (22.46 g), benzoic acid (11.8 g) and thiophene (4%, 2 ml) in methanol (440 ml) was hydrogenated with palladium-on-carbon (10%, 3 g) as a catalyst. After uptake of hydrogen (1 equivalent), the catalyst was filtered off. The filtrate was evaporated, yielding 30 g (99%) of (±)-ethyl cis-1,3,4,4a,5,9b-hexahydro-5-(phenylmethyl)-2H-pyrido[4,3-b]indole-2-carboxylate (intermediate 2).

In a similar way, (±)-ethyl cis-1,3,4,4a,5,9b-hexahydro-5-(phenylmethyl)-2H-pyrido[4,3-b]indole-2-carboxylate (intermediate 3) and (±)-ethyl cis-1,3,4,4a,5,9b-hexahydro-5-(phenylmethyl)-2H-pyrido[4,3-b]indole-2-carboxylate (intermediate 4) were prepared.

EXAMPLE A.3

A mixture of intermediate 4 (30.2 g) and potassium hydroxide (50 g) in 2-propanol (300 ml) was stirred and refluxed for 4 hours. The solvent was evaporated. Water (250 ml) was added to the residue and the organic solvent was removed by azeotropic distillation. The aqueous residue was cooled and extracted with DCM (2×200 ml). The organic layer was separated, dried, filtered and the solvent was evaporated. The residue was washed with petroleum ether (100 ml), filtered off and dried, yielding 15.5 g (65%) of (±)-cis-2,3,4,4a,5,9b-hexahydro-5-(phenylmethyl)-1H pyrido[4,3-b]indole (intermediate 5). In a similar way, (±)-cis-2,3,4,4a,5,9b-hexahydro-5-(2-phenylethyl)-1H-pyrido[4,3-b]-indole (intermediate6) and (±)-cis-2,3,4,4a,5,9b-hexahydro-5-methyl-1H-pyrido[4,3-b]-indole (intermediate 7) were prepared.

EXAMPLE A.4

A mixture of 2,3,4,5-tetrahydro-8-methoxy-2-(phenylmethyl)-1H-pyrido[4,3-b]indole monohydrochloride (39.5 g), prepared as described in *J. Org. Chem.* 44:1063–1068 (1979), in 2-methoxyethyl ether (250 ml) was stirred and cooled in an ice bath, under a $N_2$ flow. Sodium borohydride (11.7 g, solid) was added in 8 portions. The mixture was stirred overnight at room temperature, then cooled to 5° C. Ice water (500 ml) was added dropwise. Precipitation resulted. The mixture was stirred for 2 hours. The precipitate was filtered off. 1,4-Dioxane (350 ml) was added and the mixture was stirred. HCl (200 ml, 12N) was slowly added and the mixture was heated to reflux temperature. The mixture was stirred and refluxed for 1 hour, then cooled and the solvent was evaporated. The residue was stirred in water (300 ml) and this mixture was alkalized with an aqueous NaOH solution. The mixture was stirred for 1 hour. The mixture was extracted with DCM (2×200 ml). The combined extracts were dried, filtered and the solvent was evaporated. The residue was dissolved in DIPE (300 ml), then filtered and the filtrate was evaporated, yielding 11.3 g (32%) of (±)-trans-2,3,4,4a,5,9b-hexahydro-8-methoxy-2-(phenylmethyl)-1H-pyrido[4,3-b]indole (intermediate 8).

In a similar way, (±)-trans-8-chloro-2,3,4,4a,5,9b-hexahydro-2-(phenylmethyl)-1H-pyrido[4,3-b]indole (intermediate 9) was prepared.

EXAMPLE A.5

A mixture of intermediate 8 (11.3 g) in methanol (250 ml) was hydrogenated with palladium-on-carbon (10%, 2 g) as a catalyst. After uptake of hydrogen (1 equivalent), the catalyst was filtered off and the filtrate was evaporated. The residue was solidified in DIPE (30 ml). The precipitate was filtered off and dried, yielding 6.1 g (78%) of (±)-trans-2,3,4,4a,5,9b-hexahydro-8-methoxy-1H-pyrido[4,3-b]indole (intermediate 10).

EXAMPLE A.6

Sodium carbonate (20.1 g) was added to a solution of intermediate 9 (45 g) in DCM (500 ml). Ethyl chloroformate (20.6 g) was added dropwise at 5° C. The reaction mixture was stirred for 1 hour at 5° C., then for 24 hours at room temperature. More sodium carbonate (20.1 g) was added. More ethyl chloroformate (20.6 g) was added dropwise and the reaction mixture was stirred overnight at room temperature. The precipitate was filtered off and the filtrate was evaporated. The residue was suspended in petroleum ether (200 ml), decanted off and the residue was dissolved in ACN (100 ml). The compound crystallized out. The mixture was cooled to 0° C. The precipitate was filtered off and dried, yielding 26.5 g (50%) of (±)-diethyl trans-8-chloro-3,4,4a,9b-tetrahydro-2H-pyrido[4,3-b]indole-2,5(1H)-dicarboxylate (intermediate 11).

EXAMPLE A.7

Using the same reaction procedure as described in example A.3, intermediate 11 was hydrolysed to (±)-trans-8-chloro-2,3,4,4a,5,9b-hexahydro-1H-pyrido[4,3-b]indole (intermediate 12).

EXAMPLE A.8

Borane-THF complex (1:1) (400 ml) was transferred into a 4 necked flask with a syringe (under $N_2$ flow). This solution was cooled to 0° C. A solution of 2,3,4,5-tetrahydro-2-(phenylmethyl)-1H-pyrido[4,3-b]indole (52.5 g), prepared as described in J. Med. Chem. 9:436–438 (1966), in THF (400 ml) was added over a 1 hour period at 0–5° C. The reaction mixture was stirred for 1 hour at room temperature. The reaction mixture was stirred and refluxed for 4 hours, then cooled to room temperature. 6N HCl (300 ml) was added. The organic solvent was removed by evaporation. Dioxane (400 ml) was added to the residue and the mixture was stirred and refluxed for 1 hour. The solvent was evaporated. Water (300 ml) was added to the residue and this mixture was alkalized with a diluted NaOH solution. This mixture was extracted with DCM. The organic layer was separated, dried, filtered and the solvent was evaporated. The residue was purified by column chromatography over silica gel (eluent: $CHCl_3/CH_3OH$ 95/5). The pure fractions were collected and the solvent was evaporated. The residue (20 g) was crystallized from DIPE (100 ml). The crystals were filtered off and dried, yielding 7.5 g (14%) of (±)-trans-1,3,4,4a,5,9b-hexahydro-2-(phenylmethyl)-2H-pyrido[4,3-b]indole (intermediate 13).

EXAMPLE A.9

Using the same reaction procedure as described in example A.5, intermediate 13 was converted to (±)-trans-2,3,4,4a,5,9b-hexahydro-1H-pyrido[4,3-b]indole (intermediate 14).

B. Preparation of the Final Compounds.

EXAMPLE B.1

A mixture of 3-(2-chloroethyl)-2-methyl-4H-pyrido[1,2-a]pyrimidin-4-one (2.45 g), disclosed in EP-0,196,132, intermediate 5 (2.7 g), sodium carbonate (3.3 g) and potassium iodide (0.1 g) in methyl isobutyl ketone (250 ml) was stirred and refluxed for 18 hours. The reaction mixture was cooled, filtered and the filtrate was evaporated. The residue was purified by column chromatography over silica gel (eluent: $CHCl_3/CH_3OH$ 90/10). The pure fractions were collected and the solvent was evaporated. The residue was crystallized from ACN (25 ml). The crystals were filtered off and dried, yielding 2.3 g (50%) of (±)-cis-3-[2-[1,3,4,4a,5,9b-hexahydro-5-(phenylmethyl)-2H-pyrido[4,3-b]indol-2-yl]ethyl]-2-methyl-4H-pyrido[1,2-a]pyrimidin-4-one (compound 9, mp. 145.1° C.).

EXAMPLE B.2

A mixture of 6-(2-chloroethyl)-7-methyl-5H-thiazolo[3,2-a]pyrimidin-5-one (3.4 g), prepared as described in EP-A-0,070,053, intermediate 14 (2.6 g), sodium carbonate (4.8 g) and potassium iodide (0.1 g) in methyl isobutyl ketone (70 ml) was stirred for 18 hours at 90° C. The solvent was evaporated. Water (100 ml) was added and this mixture was extracted with DCM. The separated organic layer was dried, filtered and the solvent was evaporated. The residue was purified by column chromatography over silica gel (eluent: $CHCl_3/CH_3OH$ 95/5). The pure fractions were collected and the solvent was evaporated. The residue was treated with ACN (15 ml). The solid was filtered off and dried, yielding 1.5 g (28%) of (±)-trans-6-[2-(1,3,4,4a,5,9b-hexahydro-2H-pyrido[4,3-b]indol-2-yl)ethyl]-7-methyl-5H-thiazolo[3,2-a]pyrimidin-5-one (compound 11, mp. 152.5° C.).

EXAMPLE B.3

Using the same reaction procedure as described in example B.1, 6-(2-chloroethyl)-7-methyl-5H-thiazolo[3,2-a]pyrimidin-5-one (3.4 g), prepared as described in EP-A-0,070,053, was reacted with (±)-trans-8-fluoro-2,3,4,4a,5,9b-hexahydro-1H-pyrido[4,3-b]indole, prepared as described in J. Med. Chem. 22:677—(1979), to form (±)-trans-6-[2-(8-fluoro-1,3,4,4a,5,9b-hexahydro-2H-pyrido[4,3-b]indol-2-yl)ethyl]-7-methyl-5H-thiazolo[3,2-a]pyrimidin-5-one (compound 15, mp. 140.9° C.).

EXAMPLE B.4

A mixture of 6-(2-bromoethyl)-2,3-dihydro-7-methyl-5H-thiazolo[3,2-a]pyrimidin-5-one monohydrobromide (3.6 g), prepared as described in EP-0,110,435, (±)-trans-8-fluoro-5-(4-fluorophenyl)-2,3,4,4a,5,9b-hexahydro-1H-pyrido[4,3-b]indole (2.9 g), described in J. Med. Chem. 29:2093—(1986), and sodium carbonate (3.2 g) in DMF (70 ml) was stirred for 18 hours at 90° C. The cooled reaction mixture was poured out into water (400 ml) and the resulting precipitate was filtered off and dissolved in DCM (200 ml). This organic solution was washed with water (50 ml), dried, filtered and the solvent was evaporated. The residue was solidified in DIPE (50 ml), filtered off and dissolved in methanol (300 ml). The solution was treated for 30 minutes with activated charcoal. This mixture was filtered over dicalite. The filtrate was evaporated. The residue was washed in methanol (20 ml). The precipitate was filtered off, dried and purified by column chromatography over silica gel (eluent: CH₂Cl₂/CH₃OH 98/2). The pure fractions were collected and the solvent was evaporated. The residue was washed with methanol (5 ml) and dried, yielding: 1.5 g (31%) of (±)-trans-6-[2-[8-fluoro-5-(4-fluoro-phenyl)-1,3,4,4a,5,9b-hexahydro-2H-pyrido[4,3-b]indol-2-yl]ethyl]-2,3-dihydro-7-methyl-5H-thiazolo[3,2-a]pyrimidin-5-one (compound 22, mp. 110° C.).

Tables 1 and 2 list the compounds that were prepared according to one of the above Examples.

TABLE 1

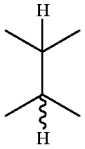

| Co. No. | Ex. No. | $R^2$ | $R^1$ | H | —$R^6$—$R^7$— | Physical data (mp. in ° C.) |
|---|---|---|---|---|---|---|
| 1 | B.2 | H | H | cis | —S—CH=CH— | mp. 165.4° C. |
| 2 | B.4 | H | H | cis | —S—CH=C(CH₃)— | mp. 149.6° C. |
| 3 | B.2 | H | H | cis | —CH=CH—CH=CH— | mp. 109.6° C. |
| 4 | B.2 | H | —CH₃ | cis | —S—CH=CH— | .HCl.2(H₂O)/ mp. 167.4° C. |
| 5 | B.1 | H | —CH₃ | cis | —CH=CH—CH=CH— | .3HCl.3/2H₂O mp. 194° C. |
| 6 | B.4 | H | —CH₃ | cis | —(CH₂)₄— | .2HCl.1/2(H₂O) mp. 210.4 °C. |
| 7 | B.1 | H | —CH₂C₆H₅ | cis | —S—CH=CH— | mp. 132.8° C. |
| 8 | B.1 | H | —CH₂C₆H₅ | cis | —S—CH₂—CH₂— | .1/2(H₂O) mp. 126.1° C. |
| 9 | B.1 | H | —CH₂C₆H₅ | cis | —CH=CH—CH=CH— | mp. 145.1° C. |
| 10 | B.1 | H | —(CH₂)₂C₆H₅ | cis | —CH=CH—CH=CH— | mp. 108° C. |
| 11 | B.2 | H | H | trans | —S—CH=CH— | mp. 152.5° C. |
| 12 | B.4 | H | H | trans | —S—CH=C(CH₃)— | mp. 215.7° C. |
| 13 | B.4 | H | H | trans | —S—CH₂—CH₂— | mp. 99.1° C. |
| 14 | B.2 | H | H | trans | —CH=CH—CH=CH— | mp. 172.8° C. |
| 15 | B.3 | F | H | trans | —S—CH=CH— | mp. 140.9° C. |
| 16 | B.1 | F | H | trans | —S—CH=C(CH₃)— | mp. 83.2° C. |
| 17 | B.2 | F | H | trans | —CH=CH—CH=CH— | mp. 193.7° C. |
| 18 | B.1 | F | H | trans | —(CH₂)₄— | mp. 203.5° C. |
| 19 | B.2 | H | —CH₃ | trans | —S—CH=CH— | .(E)-butenedioate mp. 205.0° C. |
| 20 | B.2 | H | —CH₃ | trans | —CH=CH—CH=CH— | .2HCl.H₂O mp. 240° C. |
| 21 | B.2 | H | —CH₃ | trans | —(CH₂)₄— | .2HCl mp. >260° C. |
| 22 | B.2 | F |  | trans | —S—CH=CH— | mp. 197.2° C. |
| 23 | B.3 | F |  | trans | —S—CH₂—CH₂— | mp. 110° C. |
| 24 | B.4 | F |  | trans | —S—CH=C(CH₃)— | mp. 184.7° C. |
| 25 | B.2 | F | 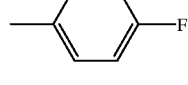 | trans | —(CH₂)₄— | mp. 145.5° C. |
| 26 | B.1 | Cl | H | trans | —S—CH=CH— | mp. 224.9° C. |

TABLE 1-continued

| Co. No. | Ex. No. | $R^2$ | $R^1$ | H (stereo) | —$R^6$—$R^7$— | Physical data (mp. in ° C.) |
|---|---|---|---|---|---|---|
| 27 | B.1 | Cl | H | trans | —S—CH=C(CH$_3$)— | mp. 201.3° C. |
| 28 | B.1 | Cl | H | trans | —CH=CH—CH=CH— | mp. 192.6° C. |
| 29 | B.1 | —OCH$_3$ | H | trans | —S—CH=CH— | mp. 201.4° C. |
| 30 | B.1 | —OCH$_3$ | H | trans | —CH=CH—CH=CH— | mp. 166.8° C. |

TABLE 2

(trans)

| Co. No. | Ex. No. | $R^2$ | $R^1$ | $R^5$ | $R^6$ | $R^7$ | Phys. data (mp. in ° C.) |
|---|---|---|---|---|---|---|---|
| 31 | B.1 | F | H | —CH$_3$ | —NHCH$_2$C$_6$H$_5$ | —CH$_3$ | mp. 96.8° C. |
| 32 | B.2 | F | —C$_6$H$_4$—F (4-fluorobenzyl) | —CH$_3$ | —NHCH$_2$C$_6$H$_5$ | —CH$_3$ | mp. 217.2° C. |
| 33 | B.2 | H | —CH$_3$ | —C$_6$H$_5$ | —CH=CH—CH=CH—* | | .2HCl.H$_2$O mp. 198.2° C. |

*: $R^6$ and $R^7$ taken together to form a bivalent radical of formula —$R^6$—$R^7$—

C. Pharmacological Example

EXAMPLE C.1

"Apomorphine, Tryptamine, Norepinephrine (ATN) Test in Rats"

The central dopamine antagonistic and serotonin antagonistic activity of the subject compounds is evidenced by the experimental data obtained in the combined apomorphine (APO), tryptamine (TRY) and norepinephrine (NOR) test in rats. Said combined apomorphine, tryptamine and norepinephrine test is described in Arch. Int. Pharmacodyn., 227, 238–253 (1977) and provides an empirical evaluation of the relative specificity with which drugs may effect particular neurotransmitter systems centrally (CNS) as well as peripherally. In this test, rats were observed for effects or responses indicating peripheral and central activity. Central dopamine antagonism is evaluated by challenging rats, subcutaneously pretreated with different doses of the test compound, with apomorphine which is a dopamine agonist. Next, serotonin antagonism is evaluated by challenging the same rats, subcutaneously pretreated with different doses of the test compound, with tryptamine which is an agonist at serotonin 5HT$_2$-receptors. Both central and peripheral serotonin antagonism can be assessed in this test. Centrally acting serotonin antagonists are potential antipsychotic drugs, in particular when simultaneously displaying dopamine antagonism in the first part of this test. Finally, α-adrenergic antagonistic activity of the test compounds is evaluated by challenging the same rats, subcutaneously pretreated with different doses of the test compound, with norepinephrine which is an α-adrenergic agonist.

The experimental data are summarized in Table 3 and expressed as ED$_{50}$ values in mg/kg body weight, which are defined as the dose at which each of the tested compounds protects 50% of the tested animals from a relevant response evoked by the above-mentioned challenging substances. Column APO lists the results of the apomorphine challenge, indicating central dopamine antagonistic activity. Column TRY convulsions and TRY hyperaemia list the results of the tryptamine challenge, indicating central and peripheral serotonin antagonistic activity respectively. Column NOR lists the results of the norepinephrine challenge, indicating α-adrenergic antagonist activity. The favourable pharmacological properties of the compounds of formula (I) lie in their potent central dopamine (column APO) and serotonin (column TRY convulsions) antagonistic activity.

TABLE 3

| Compound Number | Combined test in rats, $ED_{50}$ in mg/kg | | | |
|---|---|---|---|---|
| | APO | TRY convulsions | TRY hyperaemia | NOR |
| 11 | 0.31 | 0.31 | ≦0.04 | >10 |
| 12 | 1.25 | 1.25 | 0.02 | >10 |
| 13 | 2.5 | 5 | ≦0.04 | >10 |
| 14 | 0.31 | 1.25 | ≦0.16 | >10 |
| 15 | 0.31 | 0.31 | ≦0.0025 | >10 |
| 16 | 0.25 | 0.45 | 0.015 | >10 |
| 17 | 0.08 | 0.5 | ≦0.04 | ≧10 |
| 18 | 0.31 | 2 | 0.02 | >10 |
| 19 | 8 | 1.25 | 0.31 | 5 |
| 20 | 1.25 | 1.25 | ≦0.63 | 5 |
| 22 | 1.25 | 1.25 | 0.08 | 0.5 |
| 23 | 0.12 | 0.08 | ≦0.01 | 0.03 |
| 24 | 5 | 1.25 | ≦0.04 | 0.31 |
| 25 | 0.31 | 0.12 | 0.02 | 0.08 |
| 26 | 0.03 | 0.02 | 0.005 | >10 |
| 27 | 0.31 | 0.31 | 0.005 | >10 |
| 28 | 0.08 | 0.12 | 0.005 | >10 |
| 29 | 5 | 5 | 0.02 | ≧10 |
| 30 | ≧10 | 2 | ≦0.16 | >10 |
| 31 | 1.25 | ≧10 | ≦0.16 | >10 |

D. Composition Examples

"Active ingredient" (A.I.) as used throughout these examples relates to a compound of formula (I), a pharmaceutically acceptable addition salt or a stereochemically isomeric form thereof.

EXAMPLE D.1

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE D.2

Film-Coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

EXAMPLE D.3

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.4

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

We claim:

1. A compound of formula (I)

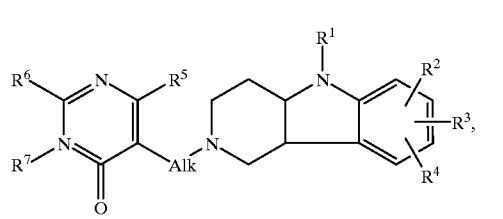

a N-oxide form, a pharmaceutically acceptable addition salt or a stereochemically isomeric form thereof, wherein Alk is $C_{1-6}$alkanediyl;

$R^1$ is hydrogen, $C_{1-6}$alkyl, aryl or aryl$C_{1-6}$alkyl;

$R^2$, $R^3$ and $R^4$ are each independently selected from hydrogen, halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl or $C_{1-6}$alkylcarbonyl;

$R^5$ is hydrogen, $C_{1-6}$alkyl, phenyl or phenyl$C_{1-6}$alkyl;

$R^6$ is hydrogen, $C_{1-6}$alkyl, $C_{1-6}$alkyloxy, $C_{1-6}$alkylthio, or a radical of formula -$NR^8R^9$, wherein $R^8$ and $R^9$ are each independently selected from hydrogen, $C_{1-6}$alkyl, phenyl or phenyl$C_{1-6}$alkyl;

$R^7$ is hydrogen or $C_{1-6}$alkyl; or $R^6$ and $R^7$ taken together may form a bivalent radical —$R^6$—$R^7$—, wherein —$R^6$—$R^7$—represents —CH$_2$—CH$_2$—CH$_2$—, (a-1)

—CH$_2$—CH$_2$—CH$_2$—CH$_2$—, (a-2)

—CH=CH—CH$_2$—, (a-3)

—CH$_2$—CH=CH— (a-4)

or

—CH=CH—CH=CH—; (a-5)

wherein one or two hydrogen atoms of said radicals (a-1) to (a-5) each independently may be replaced by halo, $C_{1-6}$alkyl, aryl$C_{1-6}$alkyl, trifluoromethyl, amino, hydroxy, $C_{1-6}$alkyloxy or $C_{1-10}$alkylcarbonyloxy; or where possible, two geminal hydrogen atoms may be replaced by $C_{1-6}$alkylidene or aryl$C_{1-6}$alkylidene; or —$R^6$—$R^7$—may also be —S—CH$_2$—CH$_2$—, (a-6)

—S—CH$_2$—CH$_2$—CH$_2$—, (a-7)

—S—CH=CH—, (a-8)

—NH—CH$_2$—CH$_2$—, (a-9)

—NH—CH$_2$—CH$_2$—CH$_2$—, (a-10)

—NH—CH=CH—, (a-11)

—NH—CH=N—, (a-12)

—S—CH=N— (a-13)

or

—CH=CH—O—; (a-14)

wherein one or where possible two or three hydrogen atoms in said radicals (a-6) to (a-14) each independently may be replaced by $C_{1-6}$alkyl or aryl; and aryl is phenyl or phenyl substituted with one, two or three substituents selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

2. A compound according to claim 1 wherein one or two hydrogen atoms of the radicals (a-1) to (a-5) each independently are replaced by $C_{1-6}$alkyl, $C_{1-6}$alkyloxy, hydroxy or $C_{1-10}$alkylcarbonyloxy; and one or where possible two hydrogen atoms in the radicals (a-6) to (a-14) each independently are replaced by $C_{1-6}$alkyl.

3. A compound according to claim 1 wherein the configuration between the hydrogen atom on carbon atom 4a and the hydrogen atom on carbon atom 9b of the hexahydro-pyrido[4,3-b]indole moiety is defined as trans.

4. A compound according to claim 1 wherein $R^6$ and $R^7$ are taken together to form a bivalent radical of formula (a1), (a-5), (a-6) or (a-8) wherein one of the hydrogen atoms may be replaced by $C_{1-6}$alkyl; and $R^5$ is phenyl or $C_{1-6}$alkyl.

5. A compound according to claim 1 wherein $R^1$ is hydrogen, $R^2$ is halo, $R^3$ and $R^4$ are both hydrogen; Alk is $C_{1-2}$alkanediyl, $R^5$ is phenyl or $C_{1-6}$alkyl; and $R^6$ and $R^7$ are taken together to form a bivalent radical of formula (a-1), (a-5), (a-6) or (a-8) wherein one of the hydrogen atoms may be replaced by $C_{1-6}$alkyl.

6. A compound according to claim 1 wherein the compound is 3-[2-(8-fluoro-1,3,4,4a,5,9b-hexahydro-2H-pyrido[4,3-b]indol-2-yl)ethyl]-2-methyl-4H-pyrido[1,2-a]pyrimidin-4-one; or 6-[2-(8-fluoro-1,3,4,4a,5,9b-hexahydro-2H-pyrido[4,3-b]indol-2-yl)ethyl]-7-methyl-5H-thiazolo[3,2-a]pyrimidin-5-one; or 6-[2-(8-chloro-1,3,4,4a,5,9b-tetrahydro-2H-pyrido[4,3-b]indol-2-yl)ethyl]-7-methyl-5H-thiazolo[3,2-a]pyrimidin-5-one; the stereoisomeric forms and the pharmaceutically acceptable addition salts thereof, or an N-oxide form thereof.

7. A pharmaceutical composition comprising a pharmaceutically acceptable carrier, and as active ingredient a therapeutically effective amount of a compound as claimed in claim 1.

8. A process of preparing a pharmaceutical composition comprising intimately mixing a therapeutically effective amount of a compound as claimed in claim 1 with a pharmaceutically acceptable carrier.

9. A method of treating a warm-blooded animal suffering from a psychotic disorder comprising administering to the warm-blooded animal a therapeutically effective amount of the compound of claim 1.

10. The method of claim 9, wherein the pyschotic disorder is schizophrenia.

* * * * *